United States Patent [19]

Robert

[11] 4,083,998
[45] Apr. 11, 1978

[54] TREATMENT OF INFLAMMATORY DISEASES OF THE MAMMALIAN LARGE INTESTINE WITH CYTOPROTECTIVE PROSTAGLANDINS

[75] Inventor: André Robert, Kalamazoo, Mich.

[73] Assignee: The Upjohn Company, Kalamazoo, Mich.

[21] Appl. No.: 658,149

[22] Filed: Feb. 17, 1976

[51] Int. Cl.² ................... A61K 31/19; A61K 31/215
[52] U.S. Cl. ..................................... 424/317; 424/305
[58] Field of Search ................................ 424/305, 317

[56] References Cited
U.S. PATENT DOCUMENTS

| | | | |
|---|---|---|---|
| 3,903,297 | 9/1975 | Robert | 424/305 |
| 3,911,124 | 10/1975 | Robert | 424/317 |
| 3,917,828 | 11/1975 | Robert | 424/317 |

Primary Examiner—Sam Rosen
Attorney, Agent, or Firm—Robert A. Armitage

[57] ABSTRACT

The present invention provides a method for treatment or prophylaxis of certain inflammatory diseases of the mammalian large intestine which comprises administrating a cytoprotective prostaglandin to a mammal who suffers from or is particularly susceptible to said inflammatory diseases of the large intestine. Cytoprotective prostaglandins refer to those prostaglandin-type compounds which are useful in reducing the incidence of NOSAC-induced lesions in the intestinal wall of the rat. "NOSAC" is an abbreviation for "nonsteroidal antiinflammatory compound."

10 Claims, No Drawings

TREATMENT OF INFLAMMATORY DISEASES OF THE MAMMALIAN LARGE INTESTINE WITH CYTOPROTECTIVE PROSTAGLANDINS

BACKGROUND OF THE INVENTION

The present invention comprises the surprising and unexpected discovery that administration of a cytoprotective prostaglandin to a mammal suffering from or particularly susceptible to certain inflammatory diseases of the large intestine provides a useful method for treatment or prophylaxis of these inflammatory diseases.

Certain pharmacological uses of prostaglandins or prostaglandin analogs in the treatment or prophylaxis of gastrointestinal tract disorders are known in the art. For example, the use of prostaglandin-type compounds effective in reducing gastric secretion and in the cure or prophylaxis of gastric or duodenal ulcers is known. See U.S. Pat. Nos. 3,903,297 and 3,781,429. Further, the concomitant use of prostaglandin-type compounds with a NOSAC (nonsteroidal antiinflammatory compound which is a prostaglandin synthetase inhibitor) is known to be effective to reduce known undesirable gastrointestinal side effects of NOSAC administration. See U.S. Pat. Nos. 3,911,124; 3,917,828; 3,928,588; and 3,927,213.

Finally, the use of $PGE_2$ to prevent damage to the gastric mucosal barrier in the dog when the gastric mucosal barrier is subjected to attack by aspirin or indomethacin is described in Gastroenterology 68:A-19/876 (April, 1975).

As used herein, the term prostaglandin refers to those cyclopentane-containing carboxylic acids derived from mammalian tissues which are structural derivatives of prostanoic acid:

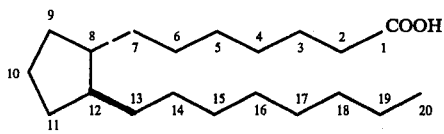

See Bergstrom, et al. Pharmacol. Rev. 20, 1 (1968) and references cited therein. For example, prostaglandin $E_2$ ($PGE_2$) exhibits the following structure:

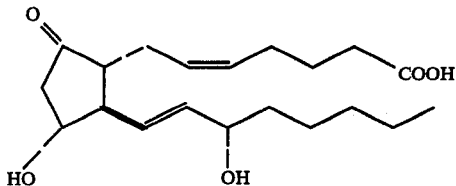

The term prostaglandin analog herein refers to those compounds structurally related to the prostaglandins (in that they exhibit a cyclopentane, or adjacently homologous cycloalkane, ring and a pair of side chains attached to adjacent carbon atoms of the ring) which retain characteristic biological properties of the prostaglandins. See Bergstrom, cited above. Various structural modifications of the prostaglandins are known to produce useful prostaglandin analogs. For example, the replacement of the carboxy with a hydroxymethyl is known, substitution of a methyl, ethyl, or fluoro for a hydrogen at, for example, C-2 or C-16, and replacement of a methylene by an oxa or thia at, for example, C-5 is known. Further, partially deoxygenated prostaglandins are known to be useful prostaglandin analogs. Accordingly, 9-deoxy, 11-deoxy, and 15-deoxy-prostaglandins are known. Finally, there are known prostaglandin analogs wherein the double bonds of, for example, $PGF_{2\alpha}$ are shifted, e.g., cis-4,5-didehydro-$PGF_{1\alpha}$, or replaced by triple bonds, e.g., 13,14-didehydro-$PGF_{2\alpha}$.

As used herein, the term prostaglandin-type compound refers to any prostaglandin or prostaglandin-analog.

The large intestine of all mammalian species is subject to a wide variety of diseases which are characterized by inflammation. For the purposes herein, these inflammatory diseases are characterized by the presence of edema, characteristic inflammatory cells (i.e., leucocytes, histiocytes, and macrophages), and in some cases necrosis and ulceration of the surface epithelium. These inflammatory diseases are readily diagnosed by conventional and readily-ascertainable means to those of ordinary skill in the art. They include, for example, colitis, ulcerative colitis, pseudomembranous colitis, inflammatory bowel disease, tropical and non-tropical sprue and diverticulitis (i.e. inflammation of diverticula).

Those inflammatory diseases are known to be caused by a number of agents which when present in the large intestine, are known to attack its walls, producing the inflammatory disease. These agents include organisms (including viruses and fungi), bacterial toxins, certain pharmaceuticals (e.g., antibiotics and anti-inflammatory steroids), noxious chemicals (e.g., bile salts, and certain household chemicals), certain foodstuffs to which susceptible mammals exhibit an allergic response (e.g., dairy products, wheat gluten, and shellfish), and parasites (e.g., amoeba helminths).

Additional causes of inflammatory diseases include radiation exposure (e.g., x-ray, $\gamma$-ray, cosmic radiation, and alpha or beta radiation, particularly when emitted from ingested radioactive materials), neoplastic growth, and invasive traumatic injury to the gut (e.g., from gunshot wounds).

Additionally, inflammatory disease is caused by a wide variety of particulate radiation, e.g., sub-atomic particles ($\pi$-mesons) and anti-matter particles (positrons), in addition to the sources described above. Accordingly, an inflammatory disease can result from radiation therapy when, for example, employed in the treatment of cancer.

Finally, the prostaglandin-type compounds are known to be useful pharmacological agents capable of conventional formulations and administration by a wide variety of routes. See U.S. Pat. No. 3,903,297 for a description of typical methods of formulation and administration.

SUMMARY OF THE INVENTION

The present invention provides a method for treating or preventing non-traumatically-induced, non-neoplastic inflammatory diseases of a mammalian large intestine which comprises:

administering to a mammal who is suffering from or highly susceptible to these inflammatory diseases an amount of a cytoprotective prostaglandin effective to cure or prevent the inflammatory disease.

In accomplishing the purposes of this invention those compounds which are useful as cytoprotective prostaglandins are those prostaglandins or prostaglandin analogs which are at least one-tenth (0.1) as potent as $PGE_2$ in effecting a 50 percent reduction in intestinal lesions in indomethacin-treated rats according to the method of A. Robert, Gastroenterology 69:1045 (1975). In accomplishing the purposes of the present invention, however, it is particularly preferred to employ those cytoprotective prostaglandins which are at least as potent as and preferably more potent than, $PGE_2$ in exhibiting intestinal lesion inhibiting properties, as described above.

The present invention relates to the treatment or prophylaxis of each of the various inflammatory diseases of the large intestine described above, except those induced by trauma or secondary to neoplastic growth. However, with respect to the latter exclusion, the present invention does provide a means whereby an inflammatory disease resulting from radiation therapy can be treated or prevented.

Further, as indicated, the present invention includes the treatment of each of the various mammalian species, including humans. With respect to non-humans, the present invention is particularly and especially concerned with treating domesticated animals, for example cattle, dogs, cats, and swine. Thus, the present invention is particularly and especially concerned with the treatment or prevention of neonatal scours in cattle and swine, coccidiosis, worms, dysentery, and inflammation of various origins (e.g. parasitic, viral, bacterial, fungal, foreign bodies).

With regard to human use, this invention, as indicated above, is useful in colitis, ulcerative colitis, pseudomembranous colitis, inflammatory bowel disease, sprue, and diverticulitis.

Any convenient route of administration is employed. Thus, oral formulation and oral administration is, for example, the preferred route for use in humans although other routes, such as via a naso-gastric tube or suppositories and enemas are employed. See. U.S. Pat. No. 3,903,297 for a description of various formulations and routes of administration encompassed in the present invention.

The dosage regimen for the cytoprotective prostaglandin in accord with this invention will depend upon a variety of factors, including the type, age, weight, sex, and medical condition of the mammal, the nature and severity of the inflammatory disease, and the particular cytoprotective prostaglandin to be administered. It is within the skill of the attending physician or veterinarian to determine the presence of the inflammatory disease, and to prescribe an effective amount of the cytoprotective prostaglandin to reduce and then substantially to eliminate the inflammation. In doing that, the physician or veterinarian would by one method start at a relatively low dose of the cytoprotective prostaglandin, for example, about 0.25 mg./kg./day to about 0.1 $\mu$g./kg./day, and observe the response of the human or animal patient for a few days. The dose of the cytoprotective prostaglandin is then adjusted downward or upward until the minimum effective dose is found. For example, the maximum needed dose is usually between about 25 mg./kg./day and about 15 $\mu$g./kg./day, although it may be necessary occasionally to exceed these doses when the inflammatory disease is especially severe. Once the minimum effective dose of the particular cytoprotective prostaglandin is determined for a particular subject, it is advantageous to provide the subject with a dosage schedule which will provide a substantially uniform level of cytoprotective prostaglandin in the wall of the large intestine.

The employment of sound medical therapy requires that the cytoprotective prostaglandin be employed prophylactically only in cases where the animal or patient is particularly susceptible to the development of an intestinal inflammatory disease. The conditions and circumstances which increase susceptibility are readily ascertainable to the ordinarily skilled physician or veterinarian, and include:

(1) long term, high dose therapy with an anti-inflammatory steroid or antibiotic;

(2) a history of colitis;

(3) a history of intestinally manifested allergic reactions; and (4) radiation therapy.

In the prophylactic use of these cytoprotective prostaglandins, the dose effective for prevention of an inflammatory disease is readily determined by the patient or animal response, as discussed above for therapeutic uses, and is, in general, somewhat less than the dose required to cure or treat the disease.

I claim:

1. A method for the treatment or prevention of a non-traumatically-induced, non-neoplastic inflammatory disease of a mammalian large intestine, which comprises:
   administering to a mammal, who is suffering from or is particularly susceptible to said inflammatory disease, an amount of a cytoprotective prostaglandin effective to cure or prevent said inflammatory disease.

2. A method according to claim 1 wherein said mammal is a human.

3. A method according to claim 2 wherein said cytoprotective prostaglandin is administered prophylactically.

4. A method according to claim 2, wherein said cytoprotective prostaglandin is administered therapeutically.

5. A method according to claim 4, wherein said inflammatory disease results from antibiotic administration.

6. A method according to claim 4, wherein said inflammatory disease results from anti-inflammatory steroid administration.

7. A method according to claim 4, wherein said inflammatory disease results from radiation exposure.

8. A method according to claim 4, wherein said inflammatory disease results from parasites.

9. A method according to claim 4, wherein said inflammatory disease results from microorganisms.

10. A method according to claim 4, wherein said cytoprotective prostaglandin is $PGE_2$.

* * * * *